(12) United States Patent
Gerhardt et al.

(10) Patent No.: US 12,343,226 B2
(45) Date of Patent: Jul. 1, 2025

(54) ORAL CARE SYSTEM FOR INTERDENTAL SPACE DETECTION

(71) Applicant: KONINKLIJKE PHILIPS N.V., Eindhoven (NL)

(72) Inventors: Lutz Christian Gerhardt, Eindhoven (NL); Mart Kornelis-Jan Te Velde, Helmond (NL); Bart Gottenbos, Budel (NL); Felipe Maia Masculo, Eindhoven (NL); Mark Thomas Johnson, Arendonk (BE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 909 days.

(21) Appl. No.: 17/604,265

(22) PCT Filed: Apr. 9, 2020

(86) PCT No.: PCT/EP2020/060168
§ 371 (c)(1),
(2) Date: Oct. 15, 2021

(87) PCT Pub. No.: WO2020/212248
PCT Pub. Date: Oct. 22, 2020

(65) Prior Publication Data
US 2022/0192807 A1     Jun. 23, 2022

(30) Foreign Application Priority Data

Apr. 16, 2019  (EP) .................................... 19169537
Jan. 28, 2020  (EP) .................................... 20154105

(51) Int. Cl.
*A61C 17/00*     (2006.01)
*A46B 5/00*      (2006.01)
(Continued)

(52) U.S. Cl.
CPC .......... *A61C 17/221* (2013.01); *A46B 5/0095* (2013.01); *A61C 17/028* (2013.01); *G16H 20/40* (2018.01)

(58) Field of Classification Search
None
See application file for complete search history.

(56) References Cited

U.S. PATENT DOCUMENTS 10,624,449 B2    4/2020   Zijlstra et al.
11,278,384 B2    3/2022   Serval
(Continued)

FOREIGN PATENT DOCUMENTS

CN      108158687 A       6/2018
DE    102008027317 A1    12/2009
(Continued)

OTHER PUBLICATIONS

International Search Report and Written Opinion Dated Jul. 7, 2020 For International Application No. PCT/EP2020/060168, Filed Apr. 9, 2020.
(Continued)

*Primary Examiner* — LaToya M Louis (57) ABSTRACT

There is provided a controller for use with an oral care device; wherein the controller is configured to estimate the location of the oral care device relative to an interdental space in a mouth using predetermined data and current use data, the current use data relating to at least one of: actions of the user during use of the oral care device, operations of the oral care device; and generate a control signal based on the outcome of the estimation. There is also provided an oral care system and a kit of parts, and a computer implemented method for an oral care device.

13 Claims, 9 Drawing Sheets

(51) Int. Cl.
*A61C 17/028* (2006.01)
*A61C 17/22* (2006.01)
*G16H 20/40* (2018.01)

(56) References Cited

U.S. PATENT DOCUMENTS

| | | | |
|---|---|---|---|
| 11,877,643 B2* | 1/2024 | Yang | A46B 15/00 |
| 2010/0309302 A1 | 12/2010 | Yang | |
| 2011/0010875 A1 | 1/2011 | Iwahori | |
| 2011/0183282 A1 | 7/2011 | Babayoff et al. | |
| 2016/0331117 A1 | 11/2016 | Follows et al. | |
| 2017/0069083 A1 | 3/2017 | Vetter et al. | |
| 2018/0125621 A1 | 5/2018 | Tweedie et al. | |
| 2019/0320785 A1 | 10/2019 | Masculo | |
| 2020/0329857 A1 | 10/2020 | Deane et al. | |
| 2021/0022840 A1 | 1/2021 | Deane et al. | |
| 2023/0028923 A1* | 1/2023 | Gharib | A61C 17/02 |
| 2023/0099863 A1* | 3/2023 | Pesach | G06V 40/165 |
| | | | 382/103 |
| 2023/0329850 A1* | 10/2023 | Serval | A46B 15/0002 |
| 2023/0386625 A1* | 11/2023 | Johnson | G16H 10/60 |
| 2024/0261073 A1* | 8/2024 | Yoshida | A61B 5/0088 |
| 2024/0268549 A1* | 8/2024 | Bevis | A46B 5/0037 |

FOREIGN PATENT DOCUMENTS

| | | |
|---|---|---|
| GB | 2538301 A | 11/2016 |
| JP | 6152604 B1 | 6/2017 |
| WO | 2018083445 A1 | 5/2018 |

OTHER PUBLICATIONS

Chen, "Computationally Efficient Carrier Integer Ambiguity Resolution in Multiepoch GPS/INS: A Common-Position-Shift Approach" IEEE Transactions on Control Systems Technology, vol. 24, No. 5, Sep. 2016 pp. 1541-1556.

Extreme Tech May 11, 2015 "Centimeter-accurate" software-based GPS positioning developed By Lendino https://www.extremetech.com/extreme/205328-centimeter-accurate-software-based-gps-positioning-developed.

* cited by examiner

ORAL CARE SYSTEM FOR INTERDENTAL SPACE DETECTION

This application is the U.S. National Phase application under 35 U.S.C. § 371 of International Application No. PCT/EP2020/060168, filed on Apr. 9, 2020, which claims the benefit of European Application Serial No. 19169537.8, filed Apr. 16, 2019 and European Application Serial No. 20154105.9, filed Jan. 28, 2020. These applications are hereby incorporated by reference herein.

FIELD OF INVENTION

This invention relates to a controller, and particularly but not exclusively a controller for use with an oral care device.

BACKGROUND OF THE INVENTION

Oral care devices now often provide functionality for interdental space flossing in addition to other functionalities of the device, such as tooth brushing. To provide a flossing functionality, fluid may be delivered through a flossing system in a toothbrush head to the teeth of a user, for example through a nozzle which is connected to a water supply in the body of the toothbrush and/or to an external water supply.

Control of flow of fluid to be delivered to the interdental spaces of the user may be achieved by manual control or by using sensors which are able to detect the location of interdental spaces, and deliver fluid when an interdental space is detected. Flossing devices are typically only effective at the interdental space. Flossing outside the interdental space has limited effectiveness and can lead to spillage of flossing fluid and undesired dispensing of liquid in the mouth. A lack of any fluid delivery control or manual control of the flossing system often leads to excessive amounts of fluid being used for flossing, and therefore wastage of fluid. However, the addition of sensors in the head of toothbrushes would result in a more complex and thus expensive brush head. Furthermore, integration of an extra sensing system, for example in the head of an oral care device, requires considerable architectural changes to the oral care device, which increases cost of the device itself or of replaceable components of the device.

SUMMARY OF THE INVENTION

According to a first aspect of an embodiment, there is provided a controller for use with an oral care device; wherein the controller is configured to estimate the location of the oral care device relative to an interdental space in a mouth using predetermined data and current use data, the current use data relating to at least one of: actions of the user during use of the oral care device, operations of the oral care device; and generate a control signal based on the outcome of the estimation.

An interdental space is a space between adjacent teeth in a mouth. The interdental space may be a gap between adjacent teeth, and/or may be an area surrounding a point of contact of adjacent teeth. The interdental space may be defined as the area bounded by a plane which is tangential to the lingual side surface of two adjacent teeth, and the region between the teeth.

The interdental space may be the interdental space in a mouth of the user of the oral care device, or may be the interdental space in a mouth of a subject other than the user of the oral care device. For example, the oral care device may be used by a healthcare professional in a mouth of a patient, or the oral care device may be used by a user in the mouth of a child or pet. The user may be the operator of the oral care device while the oral care device is used in the mouth of the user, or used in the mouth of a subject other than the user.

For example, the controller may estimate the location of a nozzle of the oral care device relative to an interdental space in a mouth. The controller may estimate the location of the oral care device relative to an interdental space in a mouth to determine if the oral care device (or a nozzle of an oral care device) is proximate (near) to and/or at (e.g. inside) an interdental space in a mouth. For example, the oral care device may be proximate to an interdental space when the distance between the oral care device (and/or centre of a nozzle of the oral care device) and the centre of an interdental space is less than a predetermined distance. When the distance between the oral care device and the interdental space is zero, the oral care device (or the nozzle, or the tip of the nozzle) may be at the interdental space. The predetermined distance may be about 50-75% of the standard width of molars/premolars (e.g. 1-1.5 cm), and/or about 50-75% of the average width of upper canines and/or incisors (e.g. 0.5-1.0 cm), and/or about 50-75% of the average width of lower incisors (e.g. 0.3-0.5 cm). The predetermined distance may be about 25-90% of the average width of molars/premolars (e.g. 0.5-1.8 cm), and/or about 25-90% of the average width of upper canine and/or incisors (e.g. 0.25-0.9 cm), and/or about 25-90% of the average width of lower incisors (e.g. 0.15-0.54 cm). For example, the oral care device may be proximate to an interdental space when the distance from the oral care device to the interdental space is, for example, less than a third (or a fourth, fifth, sixth) of the width of a standard tooth of a tooth which is closest to the oral care device. The predetermined distance may be a distance from the interdental space in a direction parallel to the teeth of a user. Alternatively or additionally, the predetermined distance may be a distance from the oral care device to the teeth, and/or an interdental space, of a user in a direction perpendicular to the teeth of a user. The distance may be an absolute value of distance.

It may be determined that an oral care device is proximate to an interdental space using electrical signals or fluid backpressure. For example, a different signal or backpressure may be detected when the oral care device is more proximate to the lingual side surface of a tooth and when the oral care device is more proximate to an interdental space.

The control signal may control the oral care device to jet fluid when it is estimated that the oral care device is proximate to, or at, an interdental space in a mouth of the user. For example, it may be estimated from the predetermined data and the current use data that the oral care device is likely to require jetting of fluid (or the like) as it is statistically likely that jetting should occur (e.g. it is likely that the oral care device is at a location of an interdental space). The oral care device may alternatively or additionally be configured to emit a powder rather than jetting fluid. For example, when the outcome of the estimation is that the oral care device is proximate to an interdental space in the mouth of a user, fluid may be jetted (or jetting may be started). When the outcome of the estimation is that the oral care device is not proximate to an interdental space in the mouth of a user, fluid may not be jetted (or jetting may be stopped).

The current use data may comprise at least one of: a position of the oral care device relative to the teeth (and/or mouth, and or/body) of the user; an orientation of the oral care device relative to the teeth (and/or mouth, and/or body) of the user; a brushing force applied to the oral care device; a drivetrain current of the oral care device; a vibration frequency of the oral care device; a strain exerted on the oral care device; a deflection of a brush head of the oral care device; a light intensity generated by or of the oral care device; a sound intensity generated by or of the oral care device; a fluid backpressure of a fluid delivery system of the oral care device; a speed or velocity of the oral care device; a fluid delivery related sensor signal. For example, current use data may be data on the way in which a user is operating the oral care device. For example, motion of the oral care device during a cleaning routine of a user may be used as current use data.

The predetermined data may be based on a correlation between location data indicating locations of interdental spaces and training use data relating to at least one of: actions of a user during use of the oral care device, operations of the oral care device. The training use data may be the same type of data as the current use data outlined above. For example, the training data may comprise at least one of: a position of the oral care device relative to the teeth of the user; an orientation of the oral care device relative to the teeth of the user; a brushing force applied to the oral care device; a drivetrain current of the oral care device; a vibration frequency of the oral care device; a strain exerted on the oral care device; a deflection of a brush head of the oral care device; a light intensity generated by or of the oral care device; a sound intensity generated by or of the oral care device; a fluid backpressure of a fluid delivery system of the oral care device; a speed or velocity of the oral care device; a fluid delivery related sensor signal.

The predetermined data may be used to determine the location of the oral care device relative to an interdental space of a user using a previous correlation between user or device behaviour and a determined location of an interdental space of a user. For example, the presence of the oral care device at, near or inside a location of an interdental space of a user may be associated with a particular angle or speed of the oral care device. When the particular angle or speed is later detected, it may then be assumed that the oral care device is once again proximate to an interdental space of a user.

The predetermined data may be at least one of: produced using a learning algorithm, based on a statistical model, based on an interdental space detection algorithm. The location data and training use data may be used as input to train a statistical model as the predetermined data. The statistical model may be used as an interdental space detection algorithm. The estimation may be based on a statistical model. Thus, the predetermined data may be usable to estimate the position of an oral care device relative to an interdental space of a user based on current use data.

According to a further aspect of an embodiment, there is provided a system comprising a device which comprises the controller. The device may be at least one of: an oral care device, a remote device, a server, a handle for an oral cleaning device. The system may further comprise at least one input device configured to obtain the location data.

The at least one input device may be comprised in at least one of: a training oral care device, a removable training head of the oral care device, a removable handle of the oral care device, a remote device, the oral care device.

The system may further comprise at least one sensor configured to obtain at least one of: current use data, training use data. At least one of the at least one sensor may be comprised in at least one of: the oral care device, a remote device, a training oral care device, a removable training head of the oral care device, a removable handle of the oral care device.

According to a further aspect of an embodiment, there is provided a kit of parts for use in an oral care system, comprising an oral care device, further comprising at least one of: a first removable head for the oral care device comprising an input device configured to collect location data relating to the location of one or more interdental spaces in a mouth, and a second removable head for the oral care device that does not comprise the input device; a first removable handle for the oral care device comprising an input device configured to collect the location data relating to the location of one or more interdental spaces in a mouth, and a second removable handle for the oral care device that does not comprise the input device; a remote device comprising an input device configured to collect the location data relating to the location of one or more interdental spaces in a mouth.

According to a further aspect of an embodiment, there is provided a training head for an oral care device for use in the system, wherein the training head comprises the input device.

According to a further aspect of an embodiment, there is provided a computer implemented method for an oral care device, the method comprising: estimating the location of the oral care device relative to an interdental space in a mouth using predetermined data and current use data, the current use data relating to at least one of: actions of a the user during use of the oral care device, operations of the oral care device; and generating a control signal based on the outcome of the estimation.

According to a further aspect of an embodiment, there may be provided a computer implemented method for producing predetermined data for use in an oral care system comprising the following steps: collecting location data on the location of one or more interdental spaces in a mouth; collecting training use data of an oral care device relating: actions of the user during use of the oral care device, operations of the oral care device during a training session; producing predetermined data relating to a correlation of the location of the interdental spaces to the training use data of the oral care device, such that the predetermined data is usable to estimate at least one of the position and orientation of the oral care device relative to the interdental spaces in a mouth of the user; and storing the predetermined data. The location data may be related to the position and/or orientation of one or more interdental spaces in a mouth. The predetermined data may be a statistical model. The predetermined data may be produced using a learning algorithm which correlates the location data to the training use data. The predetermined data may be produced using ground truth measurements in addition to the learning algorithm.

The predetermined data may comprise an interdental space detection algorithm. The predetermined data may be useable to estimate at least one of the position and orientation of an oral care device relative to the interdental spaces in a mouth of the user. The predetermined data may be usable in conjunction with current use data which is collected during use of the oral care device or another oral care device to estimate at least one of the position and orientation of an oral care device relative to the interdental spaces in a mouth of the user in use.

The method may further comprise the step of controlling the oral care device or another oral care device based on the predetermined data. The method may comprise controlling output characteristics of the device, such as fluid jetting pulses. The learning algorithm may extract fluid jetting probability and/or fluid jetting events as a function of device (and/or nozzle) orientation and/or location relative to an interdental space of a user. Thus, the oral care device may be controlled so that fluid jetting events occur with proximity of the oral care device to an interdental space of the user.

The current use data and/or the training use data may include at least one of: a position of the oral care device relative to the mouth of a user; an orientation of the oral care device relative to the mouth of a user; a brushing force applied to the oral care device; a drivetrain current of the oral care device; a vibration frequency of the oral care device; a strain exerted on the oral care device; a deflection of a brush head of the oral care device; a light intensity generated by or of the oral care device; a sound intensity generated by or of the oral care device; a fluid backpressure of a fluid delivery system of the oral care device; a speed or velocity (motion) of the oral care device, or a motion pattern produced by the device.

The remote device may be chosen from the group of remote devices comprising: a smartphone, a tablet, a computer, a remote server, a camera, or an optical tracking and scanning system.

The input device may comprise at least one of: a manual input device; a camera; a fluid pressure sensor; a velocity sensor; a force sensor; an optical distance sensor, a capacitive sensor, an electrical resistance/impedance sensor, a mechanical contact sensor, a torque sensor, an inertial measurement unit.

At least one of the input device and the sensor may comprise at least one of: a camera; a location tracking system; a fluid pressure sensor; an accelerometer; an ammeter; a force sensor; an inertial measurement unit; a tilt sensor; a brushing pressure sensor; a timer; an optical distance sensor, a capacitive sensor; GPS (Global Positioning System) or any other high-resolution navigation sensor system.

The oral care device may be chosen from the group of oral care devices comprising: a toothbrush, a flossing device, an oral irrigator, an interdental cleaning device, and a combination of these devices.

BRIEF DESCRIPTION OF THE DRAWINGS

Embodiments of the present disclosure may take form in various components and arrangements of components, and in various steps and arrangements of steps. Accordingly, the drawings are for purposes of illustrating the various embodiments and are not to be construed as limiting the embodiments. In the drawing figures, like reference numerals refer to like elements. In addition, it is to be noted that the figures may not be drawn to scale.

DETAILED DESCRIPTION OF EMBODIMENTS

The embodiments of the present disclosure and the various features and advantageous details thereof are explained more fully with reference to the non-limiting examples that are described and/or illustrated in the drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the present disclosure. The examples used herein are intended merely to facilitate an understanding of ways in which the embodiments of the present may be practiced and to further enable those of skill in the art to practice the same. Accordingly, the examples herein should not be construed as limiting the scope of the embodiments of the present disclosure, which is defined solely by the appended claims and applicable law.

Figure 1:
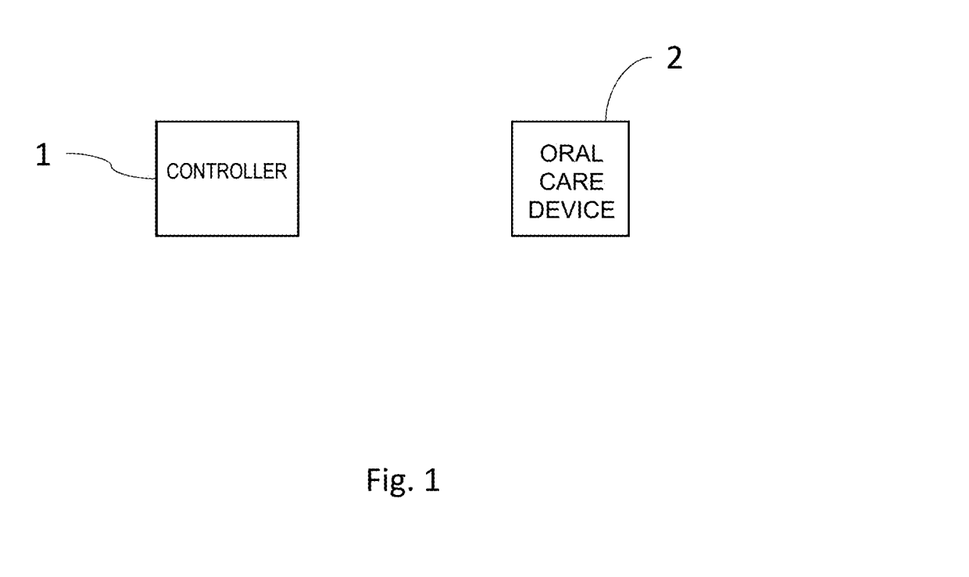
FIG. 1 illustrates a controller according to an example.

FIG. 1 illustrates a controller 1 for use with an oral care device 2 according to an example. The controller 1 may be configured to estimate the location of the oral care device 2 relative to an interdental space in a mouth using predetermined data and current use data. The current use data may relate to actions of the user during use of the oral care device and/or operations of the oral care device. The predetermined data may be input for a statistical model which is usable to estimate the location of the oral care device 2 relative to an interdental space in a mouth. The controller may also be configured to generate a control signal based on the outcome of the estimation.

For example, the controller may be configured to cause fluid to be jetted from an oral care device to perform a flossing function by generating a control signal on the basis of the predetermined data. Current use data, or data collected during normal use of the oral care device subsequent to the production of predetermined data, such as brushing forces or angles, may be collected during use of the oral care device, and used in conjunction with the predetermined data to estimate the location of the oral care device with respect to interdental spaces. Fluid jetting events of the oral care device or another oral care device may occur at the interdental spaces in accordance with the estimation. Additionally or alternatively, the control signal may control the oral care device to emit powder.

Figure 2A:
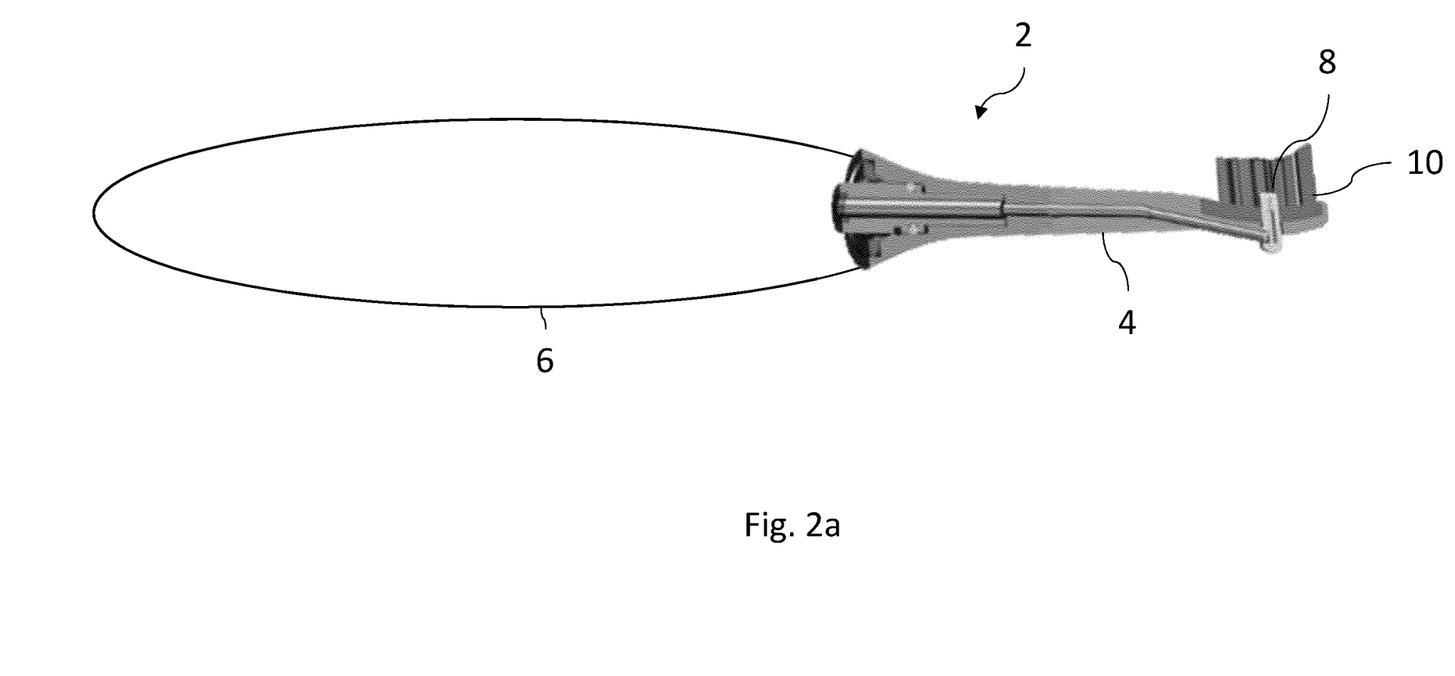
FIG. 2a illustrates an oral care device for use with the controller.

FIG. 2a is an illustration of an oral care device 2 with which the controller may be used. FIG. 2a shows a toothbrush, comprising a brush head 4 (which may be removable) and a body 6, which is configured with a jetting system for jetting fluid, and/or a system for emitting powder. The brush head 4 comprises a nozzle 8 through which fluid (e.g. water and/or gas and/or powder) may be jetted, the nozzle in this example being arranged amid bristles 10 of the brush head 4. The jetting system comprises a pump which delivers fluid from a reservoir to the nozzle (not shown), and a control unit which controls the pump and thus controls jetting events of fluid from the nozzle.

In the following description, the oral care device 2 will be described as being a tooth brush which comprises a brush head 4 with a nozzle 8 for flossing, which is capable of jetting water between the teeth of a user in use. However, it should be appreciated that the oral care device may be a toothbrush, a flossing device, an oral irrigator, an interdental cleaning device, and/or any combination of these devices, any of these devices comprising a head and/or a handle.

Figure 2B:
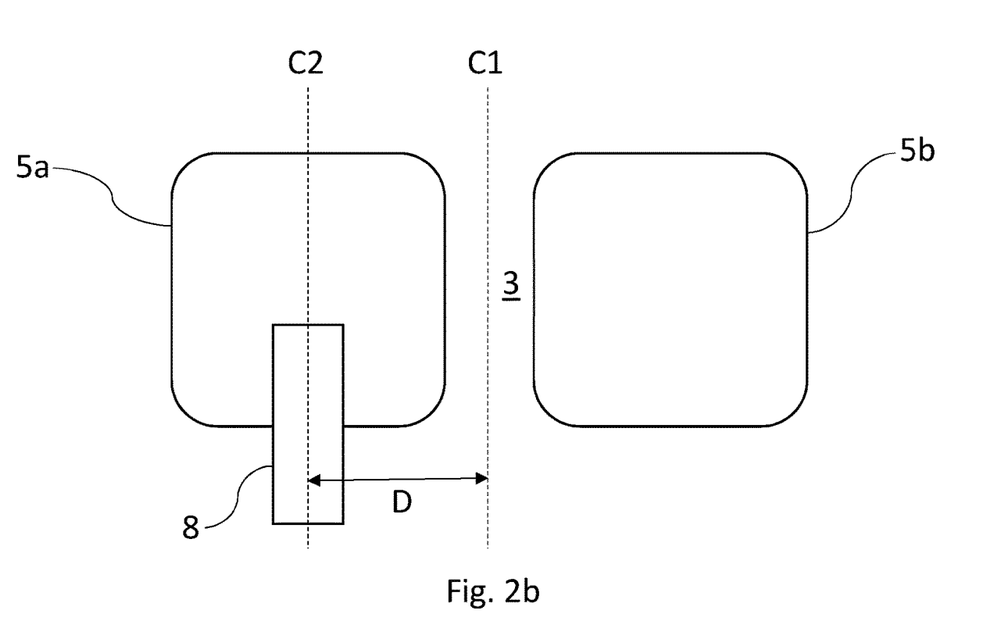
FIG. 2b illustrates a nozzle of the oral care device relative to an interdental space.

FIG. 2b illustrates the nozzle 8 of the oral care device 2 in relation to an interdental space 3. The interdental space 3 is a gap, or void, between two adjacent teeth (5a, 5b). In this example, the nozzle 8 of the oral care device 2 is positioned at the centre C2 of a first tooth 5a. The distance D from the centre of the first tooth 5a to the centre C1 of the interdental space 3 is in this example between 50-60% of the width of the first tooth. When the distance between the centre of the interdental space and the nozzle is less than 50% of the width of the first tooth 5a, the nozzle may be considered to be proximate to the interdental space. For example, when the nozzle of the oral care device is closer to the centre of the interdental space than the centre of the first tooth 5a, the nozzle may be proximate (at, or near, or in) to the interdental space.

Figure 3:
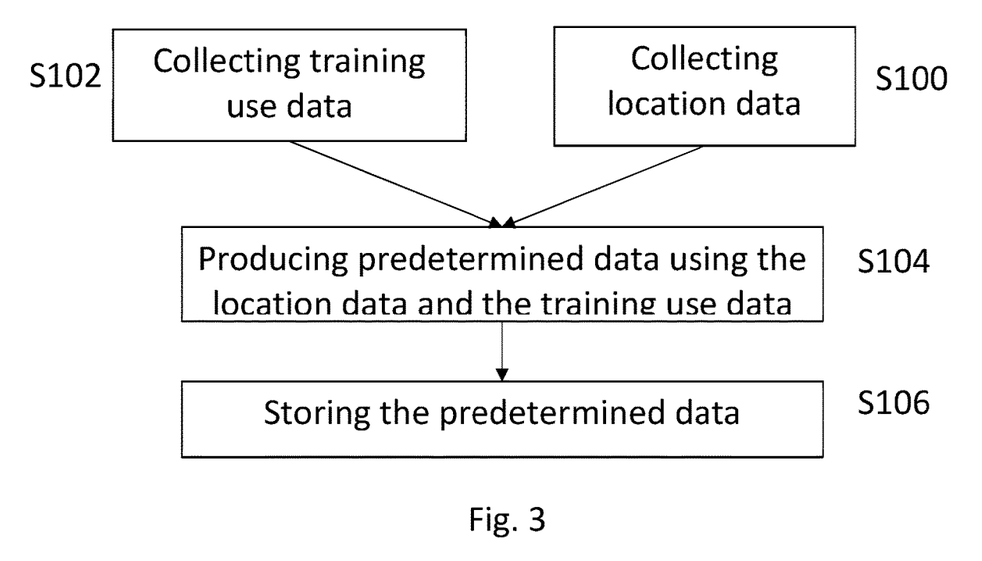
FIG. 3 illustrates a method of collecting predetermined data according to an example.

FIG. 3 illustrates a computer implemented method of training an oral care device for the detection of interdental spaces in the mouth of a user. In the method shown in FIG. 3, location data is collected which relates to the location of one or more interdental spaces in a mouth (including in-mouth device location registration) S100. The method further comprises a step of collecting training use data of an oral care device relating to actions of a user during use of the oral care device S102. The location data and the training use data are then used to produce predetermined data S104, where the predetermined data, which may be parameters of, for example, a statistical model, may then be stored (S106).

Figure 4:
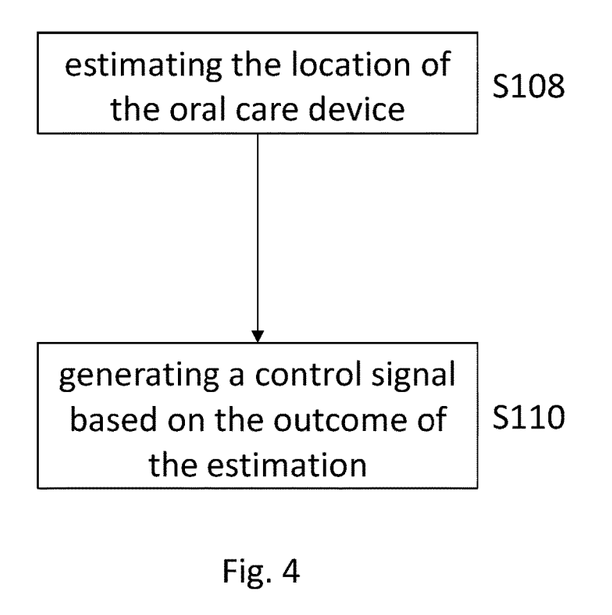
FIG. 4 illustrates a method implemented by the controller.

FIG. 4 illustrates a computer implemented method for a controller of an oral care device comprising estimating the location of the oral care device relative to an interdental space in a mouth using predetermined data and current use data, the current use data relating to at least one of: actions of a the user during use of the oral care device, operations of the oral care device; (S108) and generating a control signal based on the outcome of the estimation (S110). This method may be applied to control an oral care device to operate according to the result of the estimation. The predetermined data may be the predetermined data which has been collected in the method illustrated in FIG. 3.

Figure 5:
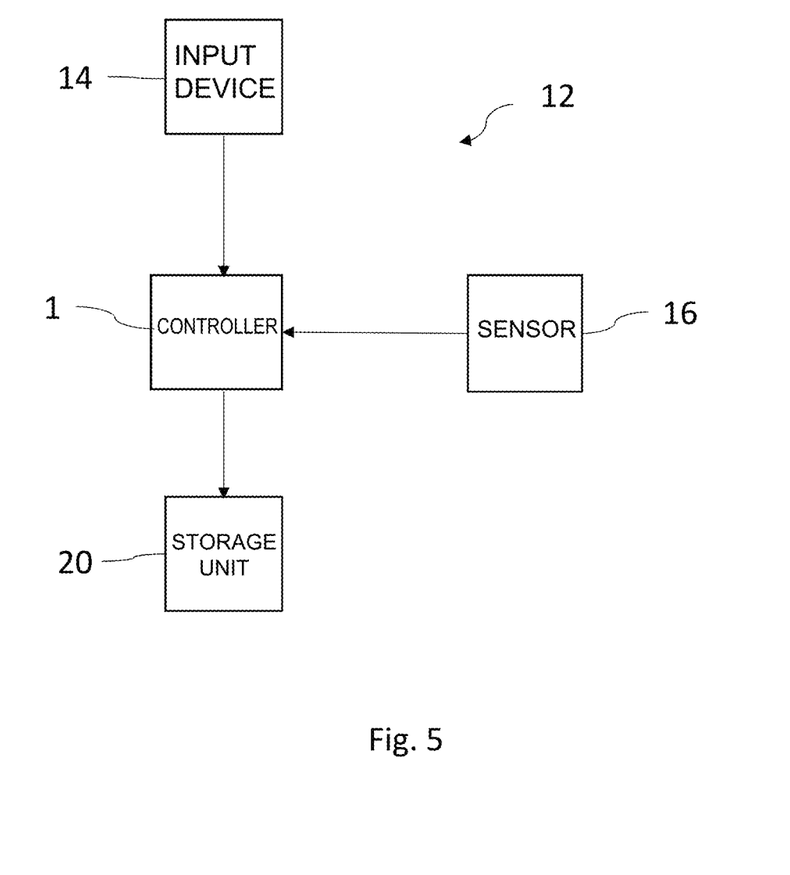
FIG. 5 illustrates a system for training an oral care system according to an example.

FIG. 5 illustrates an oral care system 12 in which the controller 1 may be comprised. The oral care system 12 comprises an input device 14 which collects the location data relating to the location of one or more interdental spaces in a mouth, and a sensor 16 which collects training use data relating to actions of a user during use of an oral care device 2. The input device and/or sensor may comprise at least one of: a camera; a location tracking system; a fluid pressure sensor; an accelerometer; an ammeter; a force sensor (which may be activated by manual input); an inertial measurement unit; a tilt sensor; a brushing pressure sensor; a timer; an optical distance sensor; a capacitive sensor; GPS; a torque sensor; a mechanical distance sensor.

The input device 14 may be comprised in a removable element of an oral care device. For example, the input device 14 maybe comprised in a removable head of an oral care device, such as a brush head. Alternatively or additionally, the input device may be comprised in a remote device, such as a smart phone. The oral care system 12 may further comprise a controller 1, which may comprise processing unit, which produces the predetermined data using (for example, correlating) the location of the interdental spaces and the training use data of the oral care device 2. The predetermined data may then be stored in a storage unit 20.

The predetermined data is usable to estimate the position of the oral care device 2 relative to the interdental spaces in a mouth of the user based on current use data which is subsequently collected (without requiring the input device 14, for example, the current use data may be collected using just the sensor 16, or an equivalent sensor). Thus, an oral care device 2 may be controlled based on the predetermined data when the input device 14 is not present or used.

Figure 6A:
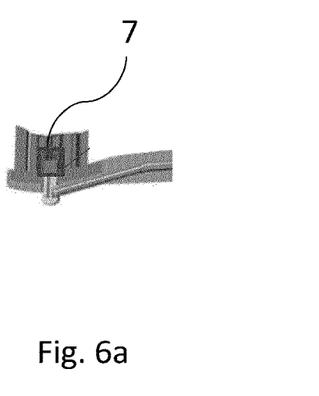
FIGS. 6a-6c illustrate alternative configuration of heads of an oral care device according to an example.
Figure 6B:
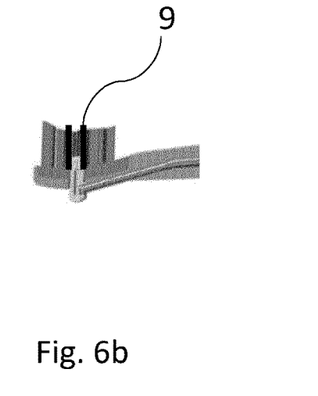
Figure 6C:
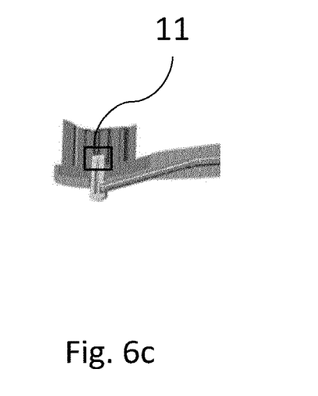

The input device may comprise an element which is configured to detect an interdental space of a user. For example, any type of sensor may be used which is capable of determining when a nozzle of the oral care device is proximate to an interdental space of a user. The input device may comprise any types of interdental space sensors working mechanically, optically, fluid back-pressure based, by sensing forces, or by any other principle. Examples of different options for configurations of the input device are shown in FIG. 6a-6c. FIG. 6a shows a sensor 7 such as those described above in or adjacent to the nozzle 8.

The user of the device or a professional may train the system by placing the nozzle 8 or a placement extension 9, which extends from the nozzle 8 and allows for more accurate determining of the location of interdental spaces relative to the nozzle 8 (as shown in FIG. 6b), on the interdental spaces, where the input device provides for input via an interface, for example where a user pushes a button when the nozzle 8 is located at an interdental space position. Data may be gathered, for example, in the first use of the oral care device 2, or in the first weeks of use.

The input device may comprise a camera 11 or any other optical (fibre) imaging method (FIG. 6c) provided in the brush head which may be used to optically inspect the teeth of a user to determine when the nozzle 8 is located at an interdental space. This determination may result in automatic jetting through the nozzle 8, or may allow a user or professional to use visual output from the camera to determine the location of the nozzle 8 within the mouth of the user, and press a button to initiate jetting when the nozzle 8 is at an interdental position.

The input device may thus comprise an imaging device (such as a camera). The imaging device may be used to take a picture of a user's teeth, externally to the mouth or inside the mouth of a user. Image analysis such as contour tracking, segmentation or thresholding of grey value images may be applied to the images to identify the location of interdental spaces in the mouth of a user. An interdental space recognition algorithm may be used to determine the location of interdental spaces from the images. A two dimensional (2D) camera may be used to take images of a user's teeth or mouth. For example, a 2D camera may be rotated to obtain a 3D image, and/or a plurality of 2D images taken of a mouth/teeth of a user could be stitched together to create a 3D image. The input device may alternatively or additionally comprise a 3D oral camera which may be used to identify interdental spaces in a mouth by imaging the inside of the mouth of a user. Reference objects with a known size may be used for scale, and/or a calibration step could be applied. For example, reference points may be used to calibrate the location of the oral care device relative to interdental spaces in a mouth.

An inertial measuring unit (IMU) may be used to measure the steps between interdental spaces using low resolution location information generated using the IMU. For example, interdental spaces may be detected from the dip in flossing/brushing velocity when the oral care device passes over an interdental space, which is detected by an IMU.

A brush head of an oral care device 2 may comprise a combination of these different input devices. For example, a camera may be used in combination with a sensor provided in or at the nozzle 8 to provide a more robust estimation of interdental spaces.

Figure 7:
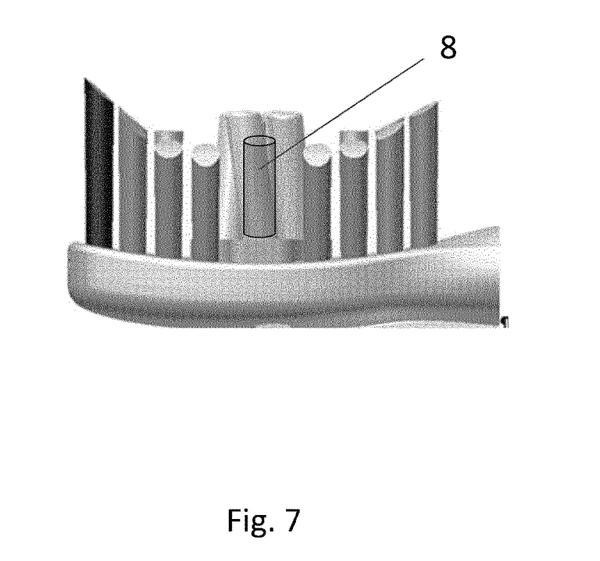
FIG. 7 illustrates a head of an oral care device for use in a training session according to examples.

A training session may be used to collect the coordinates of the interdental spaces relative to the mouth of a user using an inertial measurement unit (IMU). For such training sessions a brush head as shown in FIG. 7 may be used. The bristles or the like of the brush-head may be designed to be a shape that is a negative shape of the interdental space, to specifically increase the damping in the interdental space. The brush head of FIG. 7 comprises a nozzle 8 and features to lead the user to a stepping motion where they pause at interdental spaces when moving the brush over the teeth, in this case the features are a strong central tuft which has tilted bristles. These splay over the curved regions surfaces of teeth, but then crowd into the curvature of interdental spaces. This leads to a feeling of notching over the teeth that tends to lead to the user pausing at each interdental space. A similar effect may be achieved using the placement extension shown in FIG. 6b which extends beyond the bristles and is adjacent to the nozzle 8. Even if the user does not pause at the interdental space, the induced motion along the bristle main axis can be resolved by the IMU, and used to measure the interdental space separation.

Figure 8:
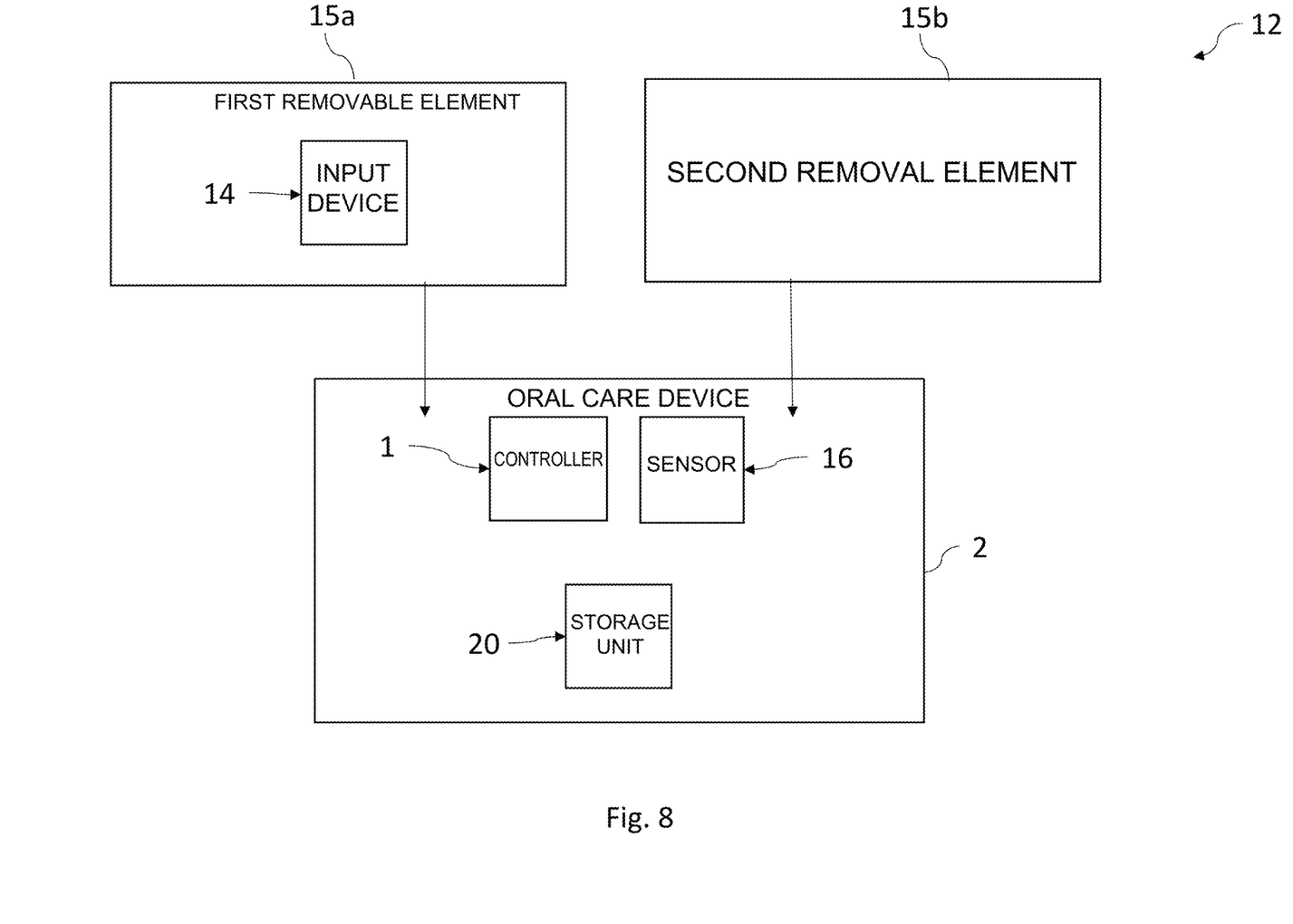
FIG. 8 illustrates a system for controlling an oral care device according to an example.

As is illustrated in FIG. 8, the oral care system 12 may comprise a first removable element 15a for use with an oral care device which comprises the input device 14, and a second removable element 15b for use with an oral care device which does not comprise the input device 14. The oral care device 2 may comprise the controller 1, storage unit 20 and sensor 16. Alternatively, any of the controller 1, storage unit 20 and sensor 16 may be provided in a remote device which is able to communicate with the oral care device 2 to control the oral care device 2. The first and second removable elements 15a, 15b may be interchangeable elements of the oral care device. For example, the removable elements may be brush heads which are operable with the oral care device. Thus, replacement parts (such as removable elements) of the oral care system may be provided at a lower cost, as expensive elements such as the input device are not required in the replacement parts to estimate whether the oral care device is proximate to an interdental space of a user.

At least a part of the oral care system may be implemented in a training oral care device, for example, a training brush head, a training body or a whole oral care device 2. For example, as is shown in FIG. 8, the input device 14 may be provided in a removable element usable with the oral care device. The oral care device may be used for training the system as a training oral care device, so that another oral care device may be controlled using the algorithm, or predetermined data, developed using the training oral care device. Thus, the predetermined data may be applied to an oral care device (or part of an oral care device) different to the oral care device 2 that was used to perform the training.

For example, the input device may be provided in a training brush head of the oral care device 2. Once predetermined data has been generated which allows the estimation of a position of an oral care device 2 relative to the interdental spaces in a mouth of the user, the input device is no longer required, as input from the sensor (the current use data) may be used with the generated predetermined data to predict the location of the one or more interdental spaces in a mouth during use. The training brush head (comprising the input device) may then be swapped for a replacement brush head which does not comprise the input device or a sensor that performs the same function as the input device. Thus, the replacement brush head may comprise no input device (used to detect interdental spaces) or fewer input devices (sensors) than that of the training brush head. The predetermined data (interdental space detection algorithm) may be used in conjunction with the replacement brush head to activate the interdental cleaning modality at the most optimal locations (e.g. in the interdental spaces) based on current use data.

By replacing a training brush head or training handle having a sensor for sensing interdental spaces with a brush head or handle without, or with fewer, sensors (for sensing interdental spaces), a more sustainable and economically efficient solution may be provided, which has the advantage that less potential waste is produced as there is less need for sensor recycling in replaceable brush heads, and replacement brush heads can be sold at lower costs as no additional sensor needed, while still keeping the advantages of having an interdental space detection modality implemented in the toothbrush. The replacement brush head may be dimensioned so that the nozzle of the replacement brush head of the oral care device 2 is positioned in substantially the same location as the nozzle 8 of the training brush head so that the algorithm developed using the training brush head is directly applicable to the replacement brush head. Alternatively or additionally, the interdental space detection algorithm may be adjusted to compensate for the difference in dimension of the replacement brush head and the training brush head.

It will be appreciated that it may be that the entire oral care device 2 does not comprise sensors or input devices which are usable to collect current use data, location data and/or training use data. The sensor which is usable to collect data may instead be provided in a remote device. For example, a camera in a smart mirror or the like may collect data on usage of the device, e.g. data relating to the location of the oral care device 2 in the mouth of a user, or data on the location of interdental spaces in the mouth of a user. This data may then be used to determine when the oral care device 2 is positioned so that the nozzle 8 is adjacent to an interdental space of the user. It will therefore be appreciated that the input device may be comprised in at least one of: a removable training head of the oral care device 2, a removable handle of the oral care device 2, a remote device, and the sensor may be comprised in at least one of: a removable training head of the oral care device 2, a removable handle of the oral care device 2, a remote device.

The predetermined data may be produced using a learning algorithm which correlates the location data to the training use data, and can therefore be used to estimate the location of oral care device relative to the interdental spaces in a mouth. For example, a machine learning algorithm may be used to link fluid jetting events of a nozzle 8 of the brush head 4 to the in-mouth brush head position (location, orientation) with respect to the gum line of the user. The fluid jetting events may be executed in response to input from a user, for example, pressing a button, and/or may be executed in response to the detection of an interdental space by an input device such as a sensor. The learning algorithm may then extract a fluid jetting probability as a function of, for example, orientation and position of the oral care device.

Various machine learning methods can be used to process the training use data and location data (for example, using a statistical model) to create predetermined data (which may be a statistical model) that is able to estimate the location of the device relative to the interdental spaces in a mouth based on the current use data. Example of such methods include using neural networks, support vector machines, k-nearest neighbour classifiers, etc. For example, the predetermined data may be a model which has been trained using the training use data and the location data. Once the model is trained, its parameters may be stored for future use, in the oral care device or, for example, in a server or a remote device. Criteria and boundary conditions for unique parameter subsets may be defined (e.g. locations of jetting events need to coincide with certain angles and forces range thresholds). During use of the device, the estimation of location of the oral care device relative to interdental spaces produced by the model are translated into binary values (0,1), representing logic states of a microprocessor/controller inside or outside the device, and used to switch one or more valves in the fluid delivery system to control jetting actions. For example, when the oral care device is estimated to be proximate to an interdental space, the binary value may be 1, and when the oral care device is estimated to not be proximate to an interdental space, the binary value may be 0. When the binary value is 1, fluid may be jetted from the oral care device, and when the binary value is 0, fluid may not be jetted from the oral care device. Methods or algorithms such as factor analysis, principle component analysis (PCA), probability distributions or multivariate regression models may also be used to create the statistical model.

The learning algorithm may thus be used to produce predetermined data comprising an interdental space detection algorithm. The interdental space detection algorithm may combine any inputs from the oral care device and/or external inputs, and determine the probability that the nozzle 8 of the oral care device 2 is at, or is proximate to, an interdental space. The oral care device may then be controlled by the controller to jet fluid. Data may be collected for use in producing the interdental space detection algorithm during training sessions performed by a user repeatedly using an oral care device 2, in which location data and/or training use data is collected. Several training sessions may be performed to collect data to create the interdental space detection algorithm. Training sessions may run over a typical recommended use time of a brush head (which may be, for example, 3 months).

Various methods may be implemented in order to produce the predetermined data. For example, the interdental space detection algorithm may be trained using in-mouth location detection from sensor signals. For example, the learning algorithm may be trained with data obtained from controlled (guided) brushing sessions with a diverse group of users or a single user. Individual head/facial characteristics data of each of the group of users or a single user may be fed into the learning algorithm as the training use data and correlated with the location of one or more interdental spaces in a mouth of each of the users. During subsequent use when current use data is collected, head/facial characteristics data detected using a sensor may thus be used as the current use data such that the location of the oral care device in the mouth of the user may be estimated using the predetermined data and the current data, and therefore determine when the oral care device is proximate to an interdental space. The interdental space detection algorithm produced as a result of the learning algorithm may thus provide a 'one size fits all' estimate of tooth segments.

Alternatively or additionally, the training use data or current use data may be produced based on motion of the oral care device during use. For example, information on a brushing motion used by a user (for example, force, velocity, angle of an oral care device) may be collected as the training use data. Subsequently, similar information collected as the current use data may be useable to determine the location of the oral care device in the mouth of the user, and thus the location of the oral care device with respect to the interdental spaces of a user.

The predetermined data may be generated by repeated use of an oral care device 2 by a user, for example, use of a brush head by a user over a three month usage cycle. During these uses, the training use data and the location data may be collected. An interdental space detection algorithm may be generated by applying AI or the like to the collected data.

The orientation of the brush head may be determined by determining the angle of the brush head with respect to dentition of a user using accelerometers. The location of the oral care device (which may be the location relative to the interdental space of the user) may be determined using GPS, for example, high resolution, sub-cm accurate GPS, which may have resolution of about 0.5-1.5 cm (covering the typical range of different tooth width such as incisors and molars). The orientation of the brush head or the location of the oral care device may be used as current use data or training use data.

Alternatively or additionally, data collected from other outputs of the oral care device may be used alone or in combination as the training use data or current use data, such as data relating to a brushing force applied to the oral care device 2, a drivetrain current of the oral care device 2, a vibration frequency of the oral care device 2, a strain exerted on the oral care device 2, a deflection of a brush head of the oral care device 2, a light intensity generated by or of the oral care device 2, a sound intensity generated by or of the oral care device 2, a fluid backpressure of a fluid delivery system of the oral care device 2, a speed or velocity of the oral care device 2. Any of these parameters may be measured by an appropriate sensor. It should be appreciated that any of these parameters may be useable to indicate the location of the oral care device with respect to interdental spaces, or a pattern of behaviour of the user while using the oral care device which may be correlated to locations of interdental spaces in the mouth of the user.

Training use data or current use data may comprise other data which is incidentally collected by the oral care device 2. For example, smart toothbrushes may collect training use data, location data and/or current use data using accelerometers and tilt sensors, as well as brushing pressure data and brushing time, as standard. Data which is collected as standard may be thus be utilised. Additionally or alternatively, further sensors which may be included in an oral care device 2 include optical distance sensors, capacitive sensors and/or high resolution GPS. Brush-head vibration damping can be assessed using motor current or brush frequency measurements, or by a sound recording system. For example, data collected using any of these systems may indicate the location of an interdental space, or may be used to improve the accuracy of detection of a location of an interdental space.

In producing the predetermined data there may be additional characteristics data fed into the learning algorithm to make the interdental space detection algorithm more robust. Characteristics data may be data on the average dentition geometry of a plurality of generic people each with certain characteristics. The characteristics data may be selected based on a comparison of personal data of a user such as gender or age, or specific personal dentition data available from a dentist relating to, for example, missing elements (e.g. teeth) or the full 3D shape of the teeth, to that of the plurality of generic people. The characteristics data may then be selected as the data which is most applicable to the characteristics of the user. This may allow for a more accurate interdental space detection.

Figure 9:
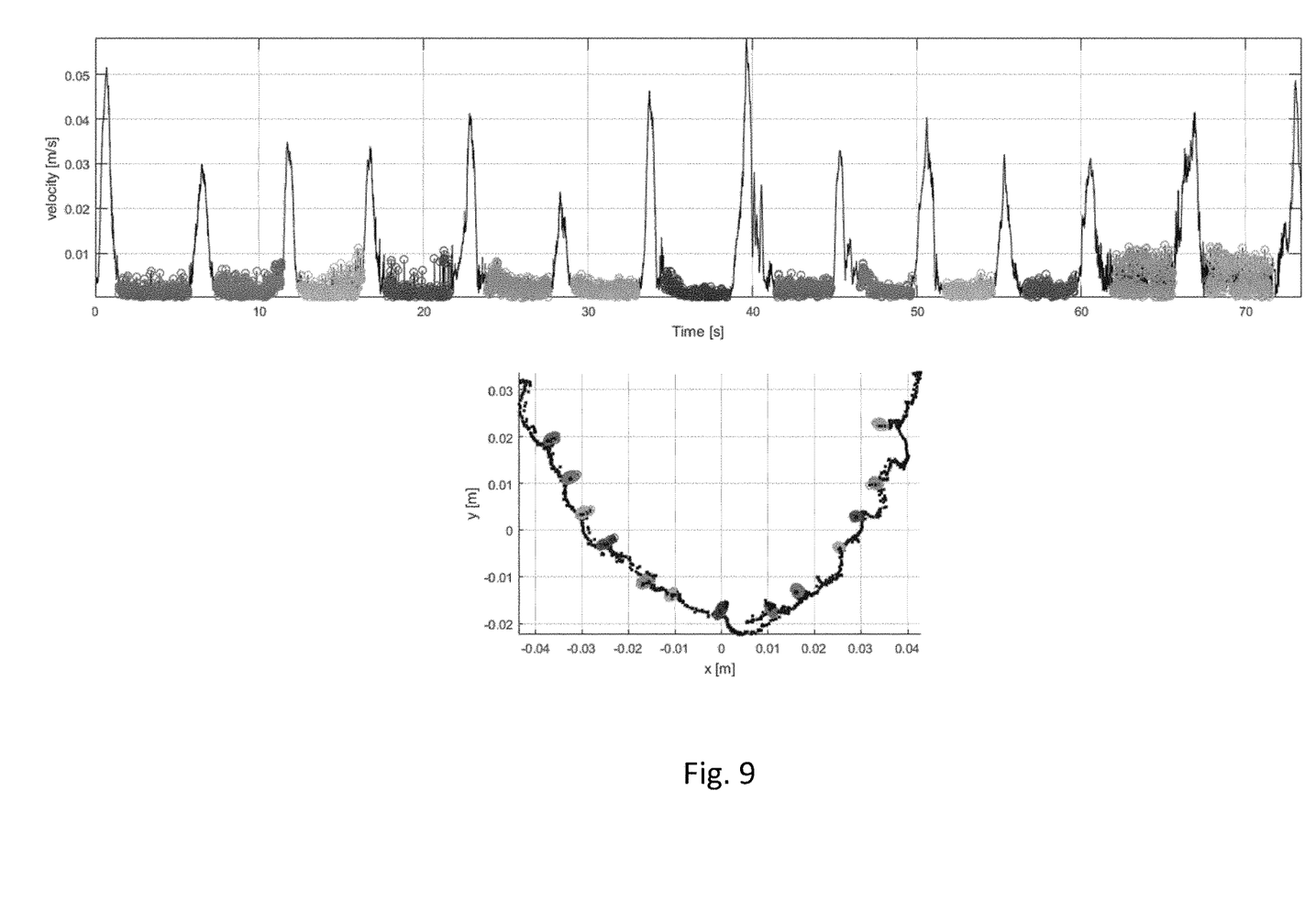
FIG. 9 shows data indicating the presence of interdental spaces in a mouth.

As discussed above, in order to identify the positions of the user's interdental spaces, one or more training sessions may be performed. For example, the user may place a probe (corresponding to the location of the nozzle 8) on each interdental space for a certain period (e.g. a few seconds) to produce tracking data indicating the motion of the probe over a period of time. Then, based on the tracking data, the probe velocity can be computed by taking the derivative of the 3D position information. The samples corresponding to interdental spaces may therefore be found by detecting the time intervals during which the probe velocity is below a certain threshold. Finally, in order to determine the coordinates of the different interdental spaces, a clustering algorithm such as k-means or hierarchical clustering may be used to find the different clusters corresponding to each interdental space. FIG. 9 shows a graph of the result of applying such algorithm to a training session, where the regions between the velocity peaks in the top graph indicate interdental spaces, and the bottom graph shows this information plotted in conjunction with information on the relative location of the oral care device at each data point.

Figure 10:
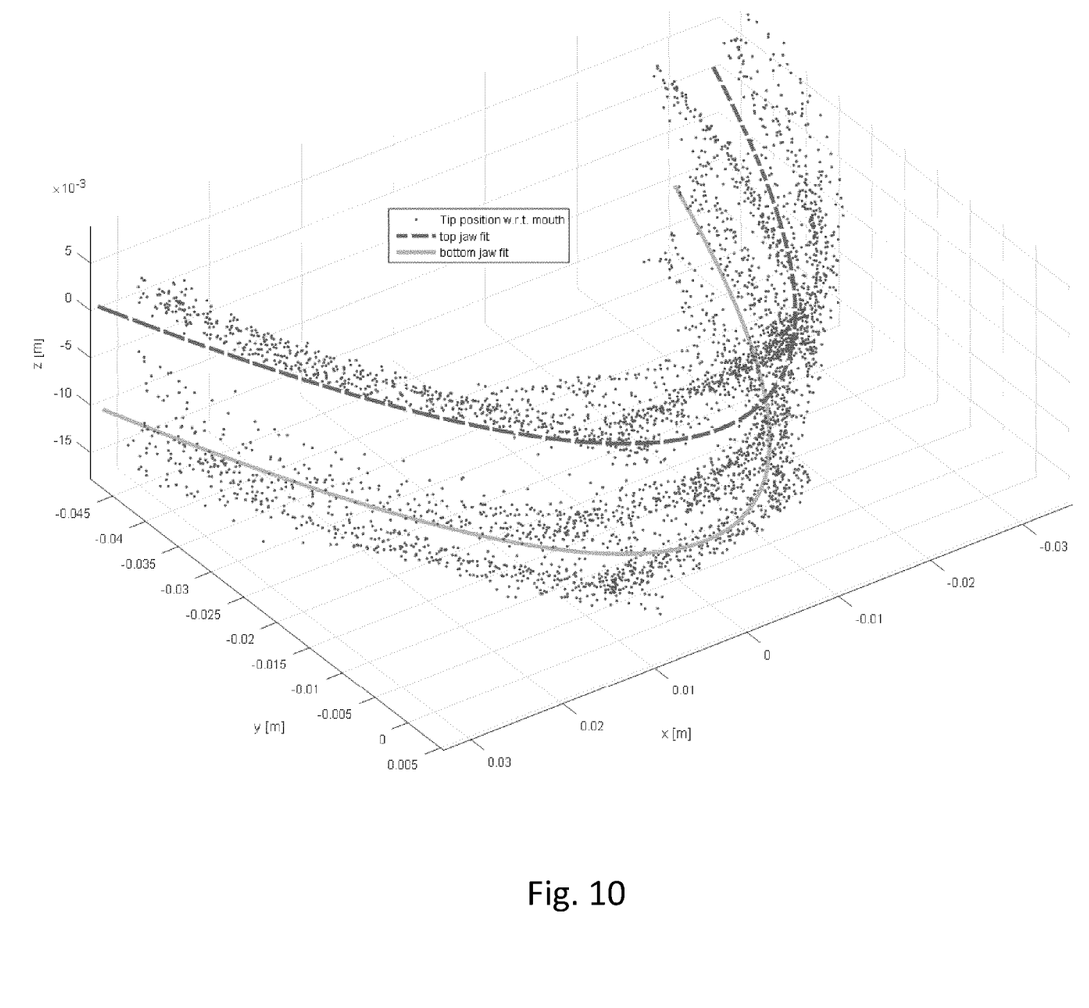
FIG. 10 shows training use data according to an example.

The training use data may be collected by a sensor 16. For example, the sensor 16 of the oral care system 12 shown in FIG. 5 may be used to determine the position of the oral care device 2 with respect to the user's mouth. As is shown in FIG. 10, the location of the brush head in the mouth of a user may be tracked with high resolution by the input device 14 during usage of the device. In FIG. 10, the dots represent individual location measurement points during usage of the device, and the bold lines are the fitted curves of these data clouds, where the shape of an upper and lower jaw of a user are clearly demonstrated by these fitted curves. This location tracking may be achieved in a number of ways, for example, using the sensors and systems described above, or by using at least one camera situated on the oral care device 2 and tracking the user's facial features so that the position of the device with respect to the mouth can be measured, and/or by using an external camera (e.g. in a smart mirror) to simultaneously track the location of the user's head and the location of the oral care device 2. Thus, the position of the device with respect to the mouth of a user can be estimated when subsequently current use data is collected.

One example of high resolution location tracking data is shown in FIG. 10 where both the position of the user's head and the position of the brush head during a training brushing session are tracked using an external camera system as the input device 14. As can be seen from this figure, the point cloud clearly follows a shape corresponding to the shape of the user's jaws. This training use data on the location of the oral care device 2 in the mouth of a user may be combined with information on the location of the interdental spaces in the mouth of the user. Current use data may be collected in the same manner.

Once the locations of the interdental spaces have been determined using the location data and the training use data, the 3D coordinates of the interdental spaces may be used to produce predetermined data for use in future cleaning sessions. During a normal (non-training) cleaning session, the device is determined to be located at an interdental space if the current use data indicates that its distance to the closest interdental space is below a certain threshold by comparison to the predetermined data.

The storage unit may be located, for example, in the oral care device 2, in an oral care device 2 used for training, in another oral care device 2 which is to be used by the user, and/or in a remote device. For example, the oral care device 2 itself may house the storage unit. Alternatively, a remote device may comprise the storage unit with the predetermined data. Information on the predetermined data or the commands for controlling an oral care device may be transmitted to an oral care device which is being used by a user, by any wireless or wired technologies, such as Wi-Fi, Bluetooth, infrared, cellular, microwave, radio etc.

In any of the above aspects, the various features may be implemented in hardware, or as software modules running on one or more processors. Features of one aspect may be applied to any of the other aspects.

The invention also provides a computer program or a computer program product for carrying out any of the methods described herein, and a computer readable medium having stored thereon a program for carrying out any of the methods described herein. A computer program embodying the invention may be stored on a computer-readable medium, or it could, for example, be in the form of a signal such as a downloadable data signal provided from an Internet website, or it could be in any other form.

It is understood that the embodiments of the present disclosure are not limited to the particular methodology, protocols, devices, apparatus, materials, applications, etc., described herein, as these may vary. It is also to be understood that the terminology used herein is used for the purpose of describing particular embodiments only, and is not intended to be limiting in scope of the embodiments as claimed. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which the embodiments of the present disclosure belong. Preferred methods, devices, and materials are described, although any methods and materials similar or equivalent to those described herein may be used in the practice or testing of the embodiments.

Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements. In a device or apparatus claim enumerating several means, several of these means may be embodied by one and the same item of hardware. The mere fact that certain measures are recited in mutually different dependent claims does not indicate that a combination of these measures cannot be used to an advantage.

Although only a few exemplary embodiments have been described in detail above, those skilled in the art will readily appreciate that many modifications are possible in the exemplary embodiments without materially departing from the novel teachings and advantages of the embodiments of the present disclosure. The above-described embodiments of the present invention may advantageously be used independently of any other of the embodiments or in any feasible combination with one or more others of the embodiments.

The invention claimed is:

1. A controller for use with an oral care device; wherein the controller is configured to:
   estimate the location of the oral care device relative to an interdental space in a mouth, using predetermined data and current use data, the current use data relating to at least one of: actions of a user during use of the oral care device, operations of the oral care device; and
   generate a control signal based on the outcome of the estimation, wherein the control signal, during use, controls the oral care device to jet fluid when it is estimated that the oral care device is proximate to or at or inside an interdental space in the mouth, wherein: the current use data comprise at least one of: a position of the oral care device relative to teeth, an orientation of the oral care device relative to teeth, a brushing force applied to the oral care device, a drivetrain current of the oral care device, a vibration frequency of the oral care device, a strain exerted on the oral care device, a deflection of a brush head of the oral care device, a light intensity generated by or of the oral care device, a sound intensity generated by or of the oral care device, a fluid backpressure of a fluid delivery system of the oral care device, a speed or velocity of the oral care device, and a fluid delivery related sensor signal; the predetermined data comprises location data indicating locations of interdental spaces and training use data relating to at least one of: actions of the user during use of the oral care device, and operations of the oral care device; and the predetermined data are based on a correlation between the location data indicating locations of interdental spaces and the training use data relating to at least one of: actions of the user during use of the oral care device, and operations of the oral care device.

2. The controller as claimed in claim 1, wherein the predetermined data is at least one of: produced using a learning algorithm, based on a statistical model, and based on an interdental space detection algorithm.

3. The controller as claimed in claim 1, wherein the estimation is based on a statistical model.

4. The controller as claimed in claim 1, wherein the device is at least one of: an oral care device, a remote device, a server, and a handle for an oral cleaning device.

5. A kit of parts for use in an oral care system, comprising an oral care device, and the controller of claim 1, further comprising at least one of:
   (i) a first removable head for the oral care device comprising an input device configured to collect location data relating to the location of one or more interdental spaces in a mouth, and a second removable head for the oral care device that does not comprise the input device;
   (ii) a first handle for receiving a head for the oral care device comprising an input device configured to collect the location data relating to the location of one or more interdental spaces in a mouth, and a second removable handle for the oral care device that does not comprise the input device; and
   (iii) a remote device comprising an input device configured to collect the location data relating to the location of one or more interdental spaces in a mouth.

6. A method for controlling an oral care device, comprising:
   estimating the location of the oral care device relative to an interdental space in a mouth using predetermined data and current use data, the current use data relating to at least one of: actions of a user during use of the oral care device, and operations of the oral care device; and
   generating a control signal based on the outcome of the estimation, wherein the control signal, during use, controls the oral care device to jet fluid when it is estimated that the oral care device is proximate to or at or inside an interdental space in the mouth, wherein: the current use data comprise at least one of: a position of the oral care device relative to teeth, an orientation of the oral care device relative to teeth, a brushing force applied to the oral care device, a drivetrain current of the oral care device, a vibration frequency of the oral care device, a strain exerted on the oral care device, a deflection of a brush head of the oral care device, a light intensity generated by or of the oral care device, a sound intensity generated by or of the oral care device, a fluid backpressure of a fluid delivery system of the oral care device, a speed or velocity of the oral care device, and a fluid delivery related sensor signal; the predetermined data comprises location data indicating locations of interdental spaces and training use data relating to at least one of: actions of the user during use of the oral care device, and operations of the oral care device; and the predetermined data are based on a correlation between the location data indicating locations of interdental spaces and training use data relating to at least one of: actions of the user during use of the oral care device, and operations of the oral care device.

7. The method of claim 6 wherein the predetermined data are at least one of: produced using a learning algorithm, based on a statistical model, and based on an interdental space detection algorithm.

8. The method of claim 6 wherein the estimation is based on a statistical model.

9. A system, comprising:
   an oral care device;
   a controller, the controller is configured to:
      estimate the location of the oral care device relative to an interdental space in a mouth, using predetermined data and current use data, the current use data relating to at least one of: actions of a user during use of the oral care device, and operations of the oral care device; and generate a control signal based on the outcome of the estimation, wherein the control signal, during use, controls the oral care device to jet fluid when it is estimated that the oral care device is proximate to or at or inside an interdental space in the mouth, wherein: the current use data comprise at least one of: a position of the oral care device relative to teeth, an orientation of the oral care device relative to teeth, a brushing force applied to the oral care device, a drivetrain current of the oral care device, a vibration frequency of the oral care device, a strain exerted on the oral care device, a deflection of a brush head of the oral care device, a light intensity generated by or of the oral care device, a sound intensity generated by or of the oral care device, a fluid backpressure of a fluid delivery system of the oral care device, a speed or velocity of the oral care device, and a fluid delivery related sensor signal; the predetermined data comprises location data indicating locations of interdental spaces and training use data relating to at least one of: actions of the user during use of the oral care device, operations of the oral care device; and the predetermined data are based on a correlation between the location data indicating locations of interdental spaces and the training use data relating to at least one of: actions of the user during use of the oral care device, and operations of the oral care device; and at least one input device configured to obtain the location data.

10. The system as claimed in claim 9, wherein the at least one input device comprises at least one of: a training oral care device, a removable training head of the oral care device, a removable handle of the oral care device, a remote device, and the oral care device.

11. The system as claimed in claim 9, further comprising at least one sensor configured to obtain at least one of: current use data, and training use data.

12. The system as claimed in claim 11, wherein at least one of the at least one sensor comprises at least one of: the oral care device, a remote device, a training oral care device, a removable training head of the oral care device, and a removable handle of the oral care device.

13. A training head for an oral care device for use in the system of claim 9, wherein the training head comprises the input device.

* * * * *